United States Patent
Makita et al.

(10) Patent No.: US 10,621,802 B2
(45) Date of Patent: Apr. 14, 2020

(54) BOARDING DOOR CONTROL SYSTEM, INFORMATION PROCESSING DEVICE, AND BOARDING DOOR CONTROL METHOD

(71) Applicant: Toyota Jidosha Kabushiki Kaisha, Toyota-shi Aichi-ken (JP)

(72) Inventors: Mitsugu Makita, Nagoya (JP); Daigo Fujii, Tsushima (JP); Naoki Yamamuro, Nagoya (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 0 days.

(21) Appl. No.: 16/273,443

(22) Filed: Feb. 12, 2019

(65) Prior Publication Data

US 2019/0251767 A1    Aug. 15, 2019

(30) Foreign Application Priority Data

Feb. 13, 2018 (JP) ................................ 2018-023159

(51) Int. Cl.
*G07C 9/00* (2020.01)
*G01N 33/00* (2006.01)

(52) U.S. Cl.
CPC ..... *G07C 9/00126* (2013.01); *G01N 33/0004* (2013.01)

(58) Field of Classification Search
CPC .................... G07C 9/00126; G01N 33/0004
USPC ........................................................ 340/5.72
See application file for complete search history.

(56) References Cited

U.S. PATENT DOCUMENTS

2002/0126054 A1* 9/2002 Fuerst ................ B60C 23/0444
                                                                    343/712
2011/0181421 A1    7/2011 Nabata et al.

FOREIGN PATENT DOCUMENTS

JP            2011155516 A        8/2011

* cited by examiner

*Primary Examiner* — Vernal U Brown
(74) *Attorney, Agent, or Firm* — Dinsmore & Shohl LLP

(57) ABSTRACT

A boarding door control system controls opening and closing of a boarding door of a vehicle. The boarding door control system includes an odor detector and an electronic control unit. The odor detector is configured to detect an odor of a user outside the vehicle. The electronic control unit is configured to, when the odor of the user outside the vehicle, detected by the odor detector, is stronger than or equal to a predetermined threshold, prohibit opening of the boarding door.

4 Claims, 5 Drawing Sheets

FIG. 5

| USER ID | SERVICE USE HISTORY | ODOR RATING |
|---|---|---|
| U001 | - D001-01 (VEHICLE ID X / BOARDING PLACE X / ALIGHTING PLACE X / RIDING TIME X / ODOR STRENGTH X)<br>- D001-02 (VEHICLE ID X / BOARDING PLACE X / ALIGHTING PLACE X / RIDING TIME X / ODOR STRENGTH X)<br>... | 98 |
| U002 | - D002-01 (VEHICLE ID X / BOARDING PLACE X / ALIGHTING PLACE X / RIDING TIME X / ODOR STRENGTH X)<br>- D002-02 (VEHICLE ID X / BOARDING PLACE X / ALIGHTING PLACE X / RIDING TIME X / ODOR STRENGTH X)<br>... | 65 |
| U003 | - D003-01 (VEHICLE ID X / BOARDING PLACE X / ALIGHTING PLACE X / RIDING TIME X / ODOR STRENGTH X)<br>- D003-02 (VEHICLE ID X / BOARDING PLACE X / ALIGHTING PLACE X / RIDING TIME X / ODOR STRENGTH X)<br>... | 87 |
| ... | ... | ... |

BOARDING DOOR CONTROL SYSTEM, INFORMATION PROCESSING DEVICE, AND BOARDING DOOR CONTROL METHOD

CROSS-REFERENCE TO RELATED APPLICATIONS

This application claims priority to Japanese Patent Application No. 2018-023159 filed on Feb. 13, 2018, which is incorporated herein by reference in its entirety including the specification, drawings and abstract.

BACKGROUND

1. Technical Field

The disclosure relates to a boarding door control system, an information processing device, and a boarding door control method.

2. Description of Related Art

In recent years, car sharing in which registered members share specific automobiles has become widespread. In car sharing, smoking in a specific vehicle may be prohibited so that no smell of cigarette sticks to the interior of the vehicle.

However, once a smell of cigarette sticks to clothes, such as clothing, it is difficult to completely remove the smell. For this reason, for example, as a smoker gets in a vehicle just after smoking, even when the smoker does not smoke inside the vehicle, a smell of cigarette that has been smoked just before getting in the vehicle sticks to the interior of the vehicle via the clothing, and the like, of the smoker.

In terms of this point, it is conceivable to employ, for example, the technique described in Japanese Unexamined Patent Application Publication No. 2011-155516 (JP 2011-155516 A). JP 2011-155516 A describes a mobile electronic device including an odor sensor, a control unit, and a microphone. The odor sensor is provided near the microphone, and detects a predetermined odor. The control unit executes a preset process when the odor sensor has detected the predetermined odor. The microphone collects words of a user. When the odor sensor has detected a smell of cigarette, the control unit transmits an e-mail to, for example, a preset communication destination.

SUMMARY

However, with the technique described in JP 2011-155516 A, it is not possible to restrict the boarding of a user having an odor stronger than or equal to a predetermined level.

The disclosure provides a boarding door control system, information processing device, and boarding door control method that are able to prevent the sticking of a smell of cigarette to the interior of a vehicle.

A first aspect of the disclosure relates to a boarding door control system. The boarding door control system controls opening and closing of a boarding door of a vehicle. The boarding door control system includes an odor detector and an electronic control unit. The odor detector is configured to detect an odor of a user outside the vehicle. The electronic control unit is configured to, when the odor of the user outside the vehicle, detected by the odor detector, is stronger than or equal to a predetermined threshold, prohibit opening of the boarding door.

According to this aspect, it is possible to restrict the boarding of a user having an odor stronger than or equal to a predetermined level. Therefore, it is possible to prevent the sticking of a smell of cigarette to the interior of a vehicle.

In the above aspect, the electronic control unit may be configured to transmit information to an information processing device via a communication network; and the information may indicate an odor strength of the odor of the user outside the vehicle, detected by the odor detector.

In the above aspect, the boarding door control system may further include a key communication unit. The key communication unit may be configured to transmit information to or receive information from an electronic key for switching between an unlocked state of the vehicle and a locked state of the vehicle. The key communication unit may be configured to extract identification information of the electronic key, included in an electronic key signal issued from the electronic key, and transmit the identification information of the electronic key to the electronic control unit. The electronic control unit may be configured to perform authentication as to whether the identification information matches identification information with which use of the vehicle is allowed; and the electronic control unit may be configured to, when both of the pieces of identification information match each other and the odor of the user outside the vehicle is stronger than or equal to the predetermined threshold, prohibit opening of the boarding door.

A second aspect of the disclosure relates to an information processing device. The information processing device is communicably connected to at least one vehicle via a communication network and used to provide service related to use of the at least one vehicle. The information processing device includes a processor. The processor is configured to receive information regarding an odor of a user outside the at least one vehicle from the at least one vehicle. The processor is configured to calculate a rating of the user based on the received information regarding the odor of the user outside the at least one vehicle.

In the above aspect, the processor may be configured to calculate a use condition of the service related to the at least one vehicle for the user associated with the rating based on the calculated rating.

A third aspect of the disclosure relates to a boarding door control method. The boarding door control method is a method of controlling opening and closing of a boarding door of a vehicle. The boarding door control method includes: detecting an odor of a user outside the vehicle; determining whether the detected odor of the user outside the vehicle is stronger than or equal to a predetermined threshold; and, when the odor is stronger than or equal to the predetermined threshold, prohibiting opening of the boarding door.

According to the aspects of the disclosure, it is possible to provide a boarding door control system, information processing device, and boarding door control method that are able to prevent the sticking of an odor of cigarette to the interior of a vehicle.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein:

FIG. 5 is a view that shows an example of an odor rating management table.

DETAILED DESCRIPTION OF EMBODIMENTS

Figure 1:
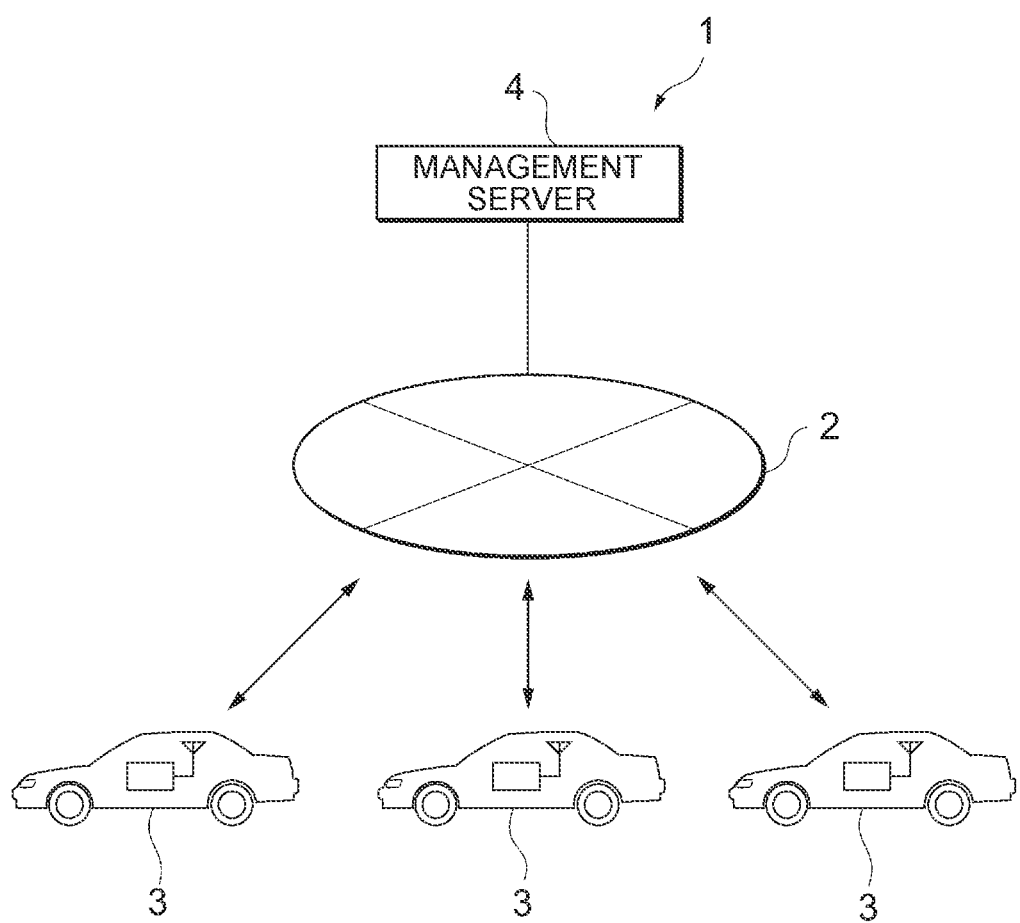
FIG. 1 is a network configuration diagram that shows an example of a car sharing system according to an embodiment of the disclosure.

An embodiment of the disclosure will be described with reference to the accompanying drawings. In the drawings, like reference numerals denote the same or similar components.

FIG. 1 is a network configuration diagram that shows an example of a car sharing system 1 according to the embodiment of the disclosure. As shown in FIG. 1, the car sharing system 1 includes at least one vehicle 3 and a management server 4 that are communicably connected to each other via a communication network 2. The management server 4 manages the provision of car sharing service. In the car sharing system 1, for example, a user is allowed to use a selected one of the at least one vehicle 3 for a predetermined period of time by carrying out communication with the management server 4 with the use of user's own information processing terminal (not shown), or the like, and, for example, applying for the service as needed.

Figure 2:
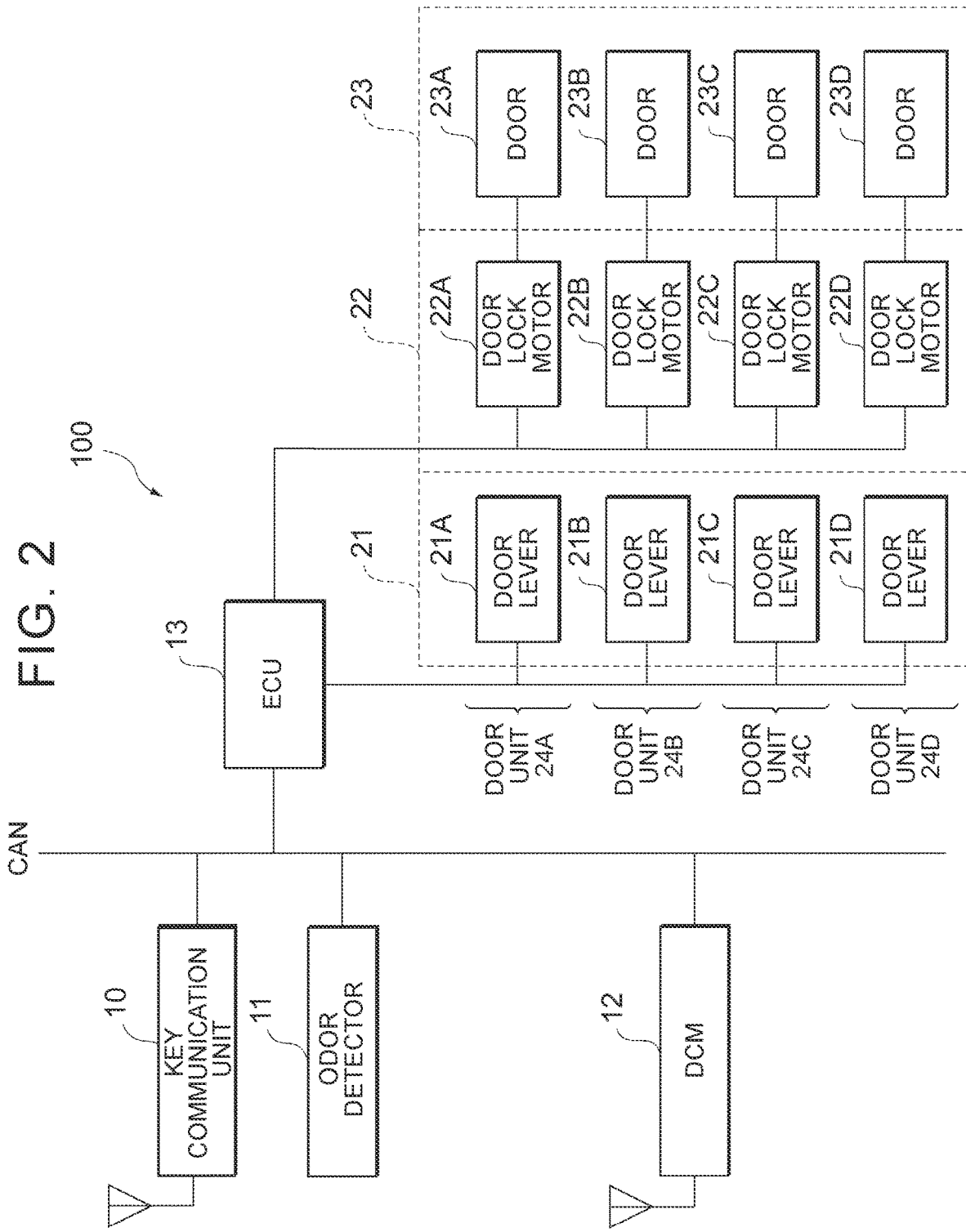
FIG. 2 is a block diagram that shows an example of a boarding door control system.

FIG. 2 is a block diagram that shows an example of a boarding door control system 100. The boarding door control system 100 is provided in each vehicle 3. The boarding door control system 100 controls opening and closing of each of boarding doors of the corresponding vehicle 3. The boarding door control system 100 includes, for example, a key communication unit 10, an odor detector 11, a data communication module (DCM) 12, an electronic control unit (ECU) 13, and door units 24. These key communication unit 10, odor detector 11, DCM 12, and ECU 13 are communicably connected to one another by an in-vehicle LAN, such as a controller area network (CAN).

The key communication unit 10 is a communication device that transmits information to or receives information from an electronic key for switching between an unlocked state and locked state of the vehicle 3. The key communication unit 10, for example, receives an electronic key signal issued from an electronic key when the user operates the electronic key, extracts identification information, and the like, of the electronic key, included in the electronic key signal, and then transmits the extracted identification information, and the like, of the electronic key to the ECU 13.

The odor detector 11 is a sensor for detecting the concentration (odor strength), and the like, of substances that smell (odorous substances), such as nicotine and tar, contained in exhalation of the user outside the vehicle. The odor detector 11 is, for example, provided at any location at which the user outside the vehicle 3 is able to breathe on the odor detector 11. The odor detector 11, for example, outputs the type and strength of a detected odor and any other information regarding the odor (odor information) to the DCM 12 and/or the ECU 13, or the like, via the CAN. The odor detector 11 may be provided at each boarding door.

The DCM 12 is a communication device for connecting to an external network, such as the communication network 2. With the DCM 12, the vehicle 3 exchanges information with the management server 4 via the communication network 2.

The DCM 12, for example, transmits, to the management server 4, odor information received from the odor detector 11.

The ECU 13 is a computer in which a CPU, a memory, a RAM, and an input/output device are connected to one another via a bus. The CPU executes programs. The memory stores the programs. The RAM is a working area in which the programs are executed. The input/output device inputs and outputs data. The ECU 13 includes a key authentication unit, an odor determination unit, a door opening prohibition unit, an odor information transmission unit, and the like, as functional modules that are implemented by programs that the CPU executes.

The key authentication unit of the ECU 13 authenticates the identification information of an electronic key received from the key communication unit 10. The authentication may be performed based on, for example, whether information received from the management server 4 in advance as the identification information of the electronic key with which the use of the vehicle 3 is allowed matches the identification information of the electronic key received from the key communication unit 10. Alternatively, the authentication may be performed by, for example, transmitting an inquiry to the management server 4 via the DCM 12 and checking whether the identification information of the electronic key matches the identification information of the electronic key with which the use of the vehicle 3 is allowed.

The odor determination unit of the ECU 13 determines whether the user outside the vehicle has exhaled or determines whether the odor is stronger than or equal to a predetermined threshold, based on the odor information received from the odor detector 11.

The door opening prohibition unit of the ECU 13 prohibits the opening of doors 23 when the odor determination unit determines that the odor is stronger than or equal to the predetermined threshold. Prohibiting the opening of the doors 23 means that door lock motors 22 are switched into a locked state and kept in the locked state when the door lock motors 22 are in an unlocked state, and the door lock motors 22 are kept in the locked state when the door lock motors 22 are in the locked state.

The odor information transmission unit of the ECU 13 transmits odor information, output from the odor detector 11, to the management server 4 via the DCM 12.

The door units 24A, 24B, 24C, 24D are respectively formed of door levers 21A, 21B, 21C, 21D (door levers 21 when the doors are not distinguished from one another), the door lock motors 22A, 22B, 22C, 22D (the door lock motors 22 when the doors are not distinguished from one another), and the doors 23A, 23B, 23C, 23D (the doors 23 when the doors are not distinguished from one another). For example, the suffix A indicates driver seat, the suffix B indicates front passenger seat, the suffix C indicates right-side rear seat, and the suffix D indicates a left-side rear seat. In the drawing, the number of the doors is four; however, the number of the doors may be any number.

Each of the doors 23 is an example of a boarding door. The boarding door is a member for opening or closing an entrance through which the user passes at the time of getting in or off the vehicle. Each door lock motor 22 is able to take at least two states in response to control that is executed by the ECU 13. The at least two states include the unlocked state where the opening of the door 23 is allowed and the locked state where the opening of the door 23 is prohibited. Each of the doors 23 has the door lever 21 at a location at which the door lever 21 is operable from the outside of the vehicle 3. When the door lock motor 22 is in the unlocked state, the user is able to open the door 23 by operating the door lever 21. When the door lock motor 22 is in the locked state, the user is not able to open the door 23 even by operating the door lever 21.

Figure 3:
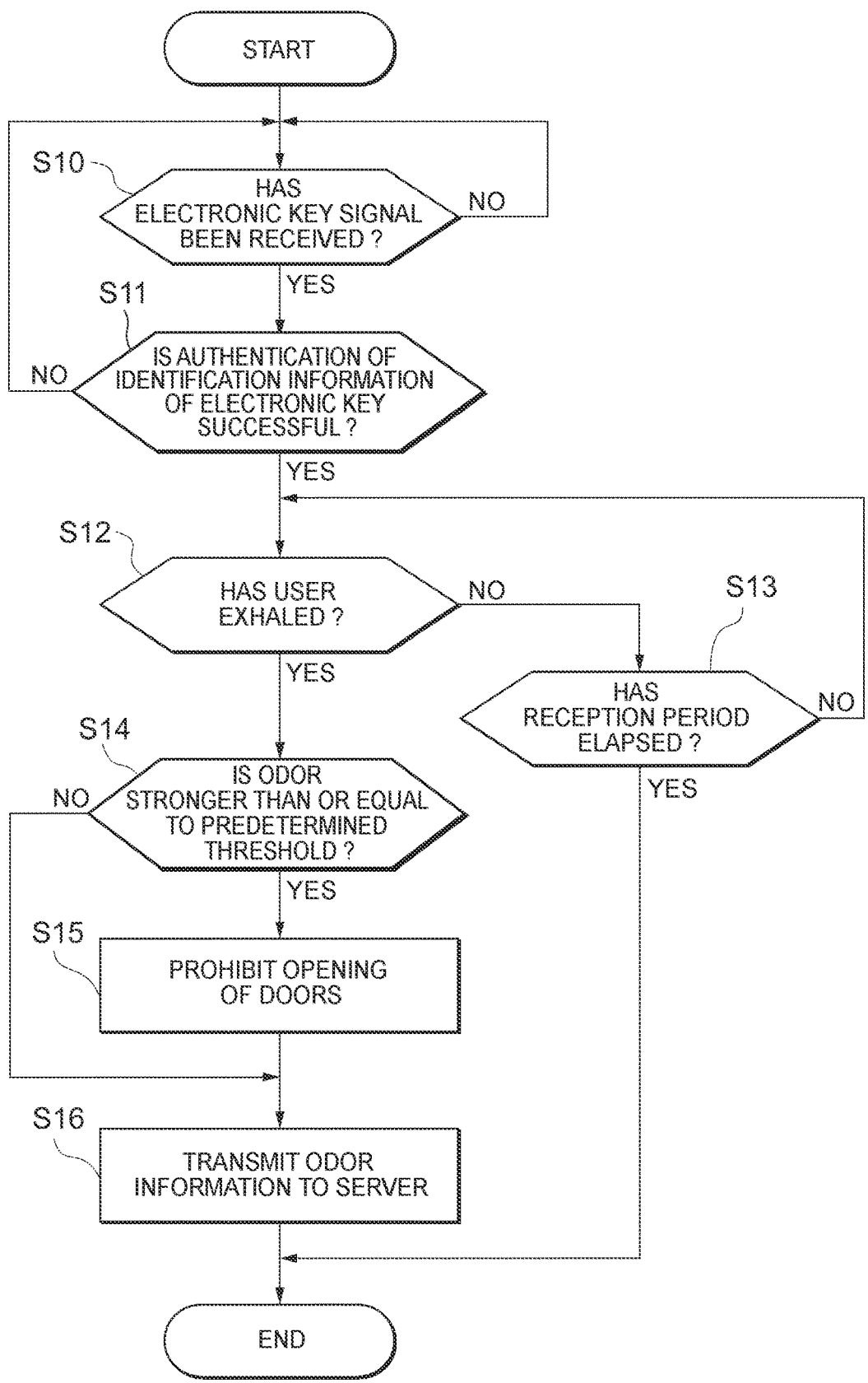
FIG. 3 is a flowchart that shows an example of operations that are executed by an ECU.

FIG. 3 is a flowchart that shows an example of operations that are executed by the ECU 13. A process according to the flowchart is executed mainly by the cooperation of the elements of the vehicle 3 based on programs stored in the vehicle 3 in advance.

Initially, the key authentication unit determines whether, for example, an electronic key signal that is issued from an electronic key held by a user outside the vehicle has been received via the key communication unit 10 (step S10). Step S10 is repeated until the electronic key signal has been received.

Subsequently, when the key authentication unit determines that the electronic key signal has been received via the key communication unit 10 (Yes in step S10), the key authentication unit executes an authentication process over the electronic key based on the identification information of the electronic key, included in the electronic key signal (step S11). As a result of the authentication process, when authentication of the identification information of the electronic key has failed (No in step S11), the process returns to step S10.

As a result of the authentication process, when authentication of the identification information of the electronic key is successful (Yes in step S11), the odor determination unit determines whether the user outside the vehicle has exhaled based on the odor information output from the odor detector 11 (step S12).

When the odor detector determines that the user outside the vehicle has not exhaled (No in step S12), the odor determination unit determines whether a predetermined period set in advance for receiving exhalation (reception period) has elapsed (step S13). As a result, the odor determination unit determines that the reception period has not elapsed (No in step S13), the process returns to step S12. On the other hand, when the odor determination unit determines that the reception period has elapsed (Yes in step S13), the process ends.

When the odor determination unit determines in step S12 that the user outside the vehicle has exhaled (Yes in step S12), the odor determination unit determines whether the odor is stronger than or equal to the predetermined threshold (step S14). When the odor determination unit determines that the odor is not stronger than or equal to the predetermined threshold (No in step S14), the process proceeds to step S16.

When the odor determination unit determines that the odor is stronger than or equal to the predetermined threshold (Yes in step S14), the door opening prohibition unit prohibits the opening of the doors 23 (step S15). Specifically, the door opening prohibition unit switches the door lock motors 22 into the locked state and keeps the locked state when the door lock motors 22 are in the unlocked state, and keeps the locked state when the door lock motors 22 are in the locked state.

Subsequently, the odor information transmission unit transmits the odor information, output from the odor detector 11, to the management server 4 via the DCM 12 (step S16). In this way, the process that is executed by the ECU 13 ends.

Figure 4:
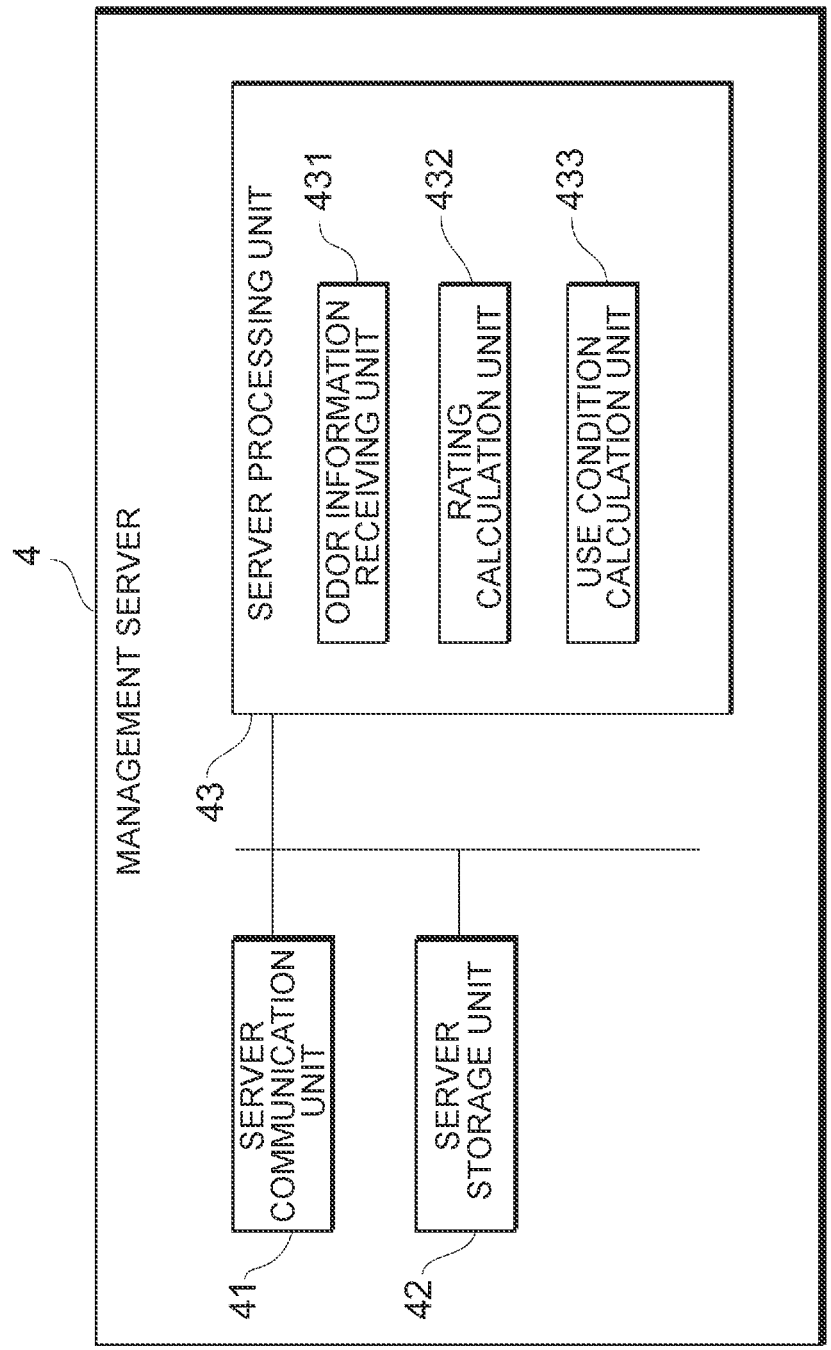
FIG. 4 is a block diagram that shows the functional configuration of a management server.

FIG. 4 is a block diagram that shows the functional configuration of the management server 4. The management server 4 is an information processing device that manages the provision of the car sharing service. The management server 4 particularly acquires odor information from each vehicle 3, calculates an odor rating that is the rating of the user based on the odor information, and uses the odor rating for the provision of the car sharing service. Therefore, the management server 4 includes, for example, a server communication unit 41, a server storage unit 42, and a server processing unit 43.

The server communication unit 41 includes a communication interface circuit for connecting the management server 4 to the communication network 2. The server communication unit 41 carries out communication with the communication network 2. The server communication unit 41 supplies the server processing unit 43 with data, such as odor information, received from each vehicle 3, and the like. The server communication unit 41 also transmits the data, supplied from the server processing unit 43, to each vehicle 3, and the like.

The server storage unit 42 includes, for example, at least one of a magnetic tape device, a magnetic disk device, and an optical disk device. The server storage unit 42 stores computer programs (an operating system program, driver programs, and application programs), data (including temporary data regarding a predetermined process), and the like. The computer programs are used to execute processes in the server processing unit 43. For example, the server storage unit 42 stores a program, and the like, related to the provision of the car sharing service as an application program. The computer programs may be installed from a computer-readable portable recording medium, such as a CD-ROM and a DVD-ROM, to the server storage unit 42 with the use of a known setup program, or the like.

The server storage unit 42, for example, stores an odor rating management table shown in FIG. 5 as data. The odor rating management table is a data table for managing a riding history and odor rating of each user. Information, such as user ID, service use history, and odor rating, is stored in the odor rating management table in association with one another user by user. The user ID is information for identifying a user. The service use history is information regarding the use of the car sharing service in the past. The service use history includes, for example, riding ID (indicated as D001-01, or the like, in FIG. 5), vehicle ID, boarding place, alighting place, riding time, odor strength, and the like. The riding ID is information for identifying a ride in a vehicle 3 associated with the use of the service. The vehicle ID is information for identifying a riding vehicle 3. The odor strength is information that indicates the odor strength of the user, detected by the odor detector 11 of a vehicle 3. The odor rating is, for example, information that indicates the rating of the user, calculated by a rating calculation unit 432 of the server processing unit 43 based on the odor strength included in the service use history.

The server processing unit 43 includes at least one processor and its peripheral circuit. The server processing unit 43 is, for example, a CPU, and generally controls the overall operations of the management server 4. The server processing unit 43 controls the operations of the server communication unit 41, and the like, such that various processes of the management server 4 are executed in an appropriate procedure based on the programs, and the like, stored in the server storage unit 42. The server processing unit 43 executes processes based on the programs (operating system program, driver programs, application programs, and the like) stored in the server storage unit 42.

The server processing unit 43 includes an odor information receiving unit 431, the rating calculation unit 432, and a use condition calculation unit 433. These units are functional modules that are implemented by programs that are executed on the at least one processor of the server processing unit 43.

The odor information receiving unit 431 receives odor information transmitted from each vehicle 3 via the communication network 2, and stores the odor information in the odor rating management table stored in the server storage unit 42.

The rating calculation unit 432 calculates an odor rating that is the rating of a user with a predetermined method based on the odor information. The method of calculating an odor rating is not specifically limited. For example, the odor rating may be the average of odor strengths acquired in a predetermined period in the past. The rating may be calculated by varying weights depending on the time at which the strength of odor is acquired and then adding up the strengths of odor in a predetermined period.

The use condition calculation unit 433 calculates the use condition of the car sharing service, unique to a user, based on the odor rating. Elements of the use condition are not specifically limited. For example, the elements may include a usable vehicle model, a usable shop, usable day and time period, a usage fee, a minimum use time, a maximum use time, amenities to be provided during use, and the like.

According to the present embodiment, since opening a door of a vehicle is prohibited when the odor inside the vehicle is stronger than or equal to a predetermined threshold, it is possible to restrict the boarding of a user having an odor stronger than or equal to a predetermined level. Therefore, it is possible to prevent the sticking of a smell of cigarette to the interior of a vehicle.

What is claimed is:

1. A boarding door control system that controls opening and closing of a boarding door of a vehicle, the boarding door control system comprising:
    an odor detector configured to detect an odor of a user outside the vehicle; and
    an electronic control unit configured to, when the odor of the user outside the vehicle, detected by the odor detector, is stronger than or equal to a predetermined threshold, prohibit opening of the boarding door.

2. The boarding door control system according to claim 1, wherein:
    the electronic control unit is configured to transmit information to an information processing device via a communication network; and
    the information indicates an odor strength of the odor of the user outside the vehicle, detected by the odor detector.

3. The boarding door control system according to claim 1, further comprising a key communication unit configured to transmit information to or receive information from an electronic key for switching between an unlocked state of the vehicle and a locked state of the vehicle, the key communication unit being configured to extract identification information of the electronic key, included in an electronic key signal issued from the electronic key, the key communication unit being configured to transmit the identification information of the electronic key to the electronic control unit, wherein:
    the electronic control unit is configured to perform authentication as to whether the identification information matches identification information with which use of the vehicle is allowed; and
    the electronic control unit is configured to, when both of the pieces of identification information match each other and the odor of the user outside the vehicle is stronger than or equal to the predetermined threshold, prohibit opening of the boarding door.

4. A boarding door control method of controlling opening and closing of a boarding door of a vehicle, the boarding door control method comprising:
    detecting an odor of a user outside the vehicle;
    determining whether the detected odor of the user outside the vehicle is stronger than or equal to a predetermined threshold; and
    when the odor is stronger than or equal to the predetermined threshold, prohibiting opening of the boarding door.

* * * * *

UNITED STATES PATENT AND TRADEMARK OFFICE
CERTIFICATE OF CORRECTION

| | |
|---|---|
| PATENT NO. | : 10,621,802 B2 |
| APPLICATION NO. | : 16/273443 |
| DATED | : April 14, 2020 |
| INVENTOR(S) | : Mitsugu Makita, Daigo Fujii and Naoki Yamamuro |

Page 1 of 1

It is certified that error appears in the above-identified patent and that said Letters Patent is hereby corrected as shown below:

On the Title Page

Item (72), inventor 1, city, delete "Nagoya" and insert --Nagoya-shi Aichi-ken--, therefor.

Item (72), inventor 2, city, delete "Tsushima" and insert --Tsushima-shi Aichi-ken--, therefor.

Item (72), inventor 3, city, delete "Nagoya" and insert --Nagoya-shi Aichi-ken--, therefor.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*